United States Patent [19]

Kubo

[11] Patent Number: 5,364,788
[45] Date of Patent: Nov. 15, 1994

[54] **PURE CULTURE OF *BACILLUS SUBTILIS* FERM BP-3418**

[75] Inventor: Kazuhiro Kubo, Maebashi, Japan

[73] Assignee: AHC Inc., Maebashi, Japan

[21] Appl. No.: 906,460

[22] Filed: Jun. 30, 1992

[30] Foreign Application Priority Data

Jul. 1, 1991 [JP] Japan ................... 3-185880
Jan. 8, 1992 [JP] Japan ................... 4-018434

[51] Int. Cl.$^5$ .............. A01N 63/00; A01N 25/00; A01N 25/34; C12N 1/20
[52] U.S. Cl. ................... 435/252.5; 424/404; 424/405; 424/93.462; 424/93.7; 435/839
[58] Field of Search ............... 435/252.5, 839; 424/93, 424/93 M, 93 U, 404, 405

[56] References Cited

U.S. PATENT DOCUMENTS

| | | | |
|---|---|---|---|
| 3,980,050 | 9/1976 | Neubauer | 119/1 |
| 4,085,224 | 4/1978 | Berg et al. | 424/283 |
| 4,323,565 | 4/1982 | Hasegawa et al. | 424/246 |
| 4,764,371 | 8/1988 | Pusey et al. | 424/93 |
| 4,931,398 | 6/1990 | Kimura | 435/252.5 |
| 5,045,464 | 9/1991 | Ito et al. | 435/209 |
| 5,047,239 | 9/1991 | Pusey | 424/93 |
| 5,215,747 | 6/1993 | Hairston et al. | 424/93 M |

OTHER PUBLICATIONS

Database WPIL, Derwent Publications Ltd., AN 88-307567, & WO-A-8 808 031, Oct. 20, 1988, "Cyclodextrin Glycosyltransferase-Prepd. by culturing *Bacillus licheniformis* Strain".

Patent Abstracts of Japan, vol. 013, No. 171, 1989, & JP-A-64 002 570, 1989, Kimura Nobuo, "Bacillus . . . Subtilis Strain and Elimination of . . . Aflatoxin . . . Contamination Using Said Strain".

Database WPIL, Derwent Publications Ltd., AN 82-08085J, & JP-A-57 180 498, 1982, "Deodorised . . . Fermented . . . Prod. Prepd. from Animal Fodder and-/or Wastes-by Inoculating with Bacilli Contg. Carbohydrate- and Protein-Hydrolysing Enzyme(s)".

Database WPIL, Derwent Publications, Ltd., AN 83-37272K, & EP-A-76 642, 1983, "Denitrification of Tobacco-Using Thermophilic Anaerobic Microorganism".

Database WPIL, Derwent Publications, Ltd., AN 85-267242, & JP-A-60 180 589, 1985, "Fixed Complex of Microorganisms-Which is Resistant of Phytopathogenic Microorganisms".

Chemical Abstracts, vol. 102, No. 17, Abstract No. 147673e, O. A. Kirilenko, et al., "Effect of Relative Air Humidity and Accompanying Microflora on Aflatoxin Formation in Food Concentrates".

Database WPIL, Derwent Publications, Ltd., AN 89-209275, & JP-A-1 144 971, 1989, "Microbe for Sewage Disposal and . . . Deodorisation . . . In . . . *Bacillus subtilis* Kubota having Specified Mycological Properties".

Database WPIL, Derwent Publications, Ltd., AN 88-271159, & WO-A-806 619, 1988, "Compsns. for Control of Animal Gastorintestinal Disorders-Contg. Selected Strains of *Bacillus subtilis* and . . . Licheniformis".

Database WPIL, Derwent Publications, Ltd., AN 83-744559, JP-A-58 120 585, 1983, "Fertiliser Prodn. from Fish and Animal Waste-by Adding Cyanamide Lime, Opt. Neutralising, Resistance Heating in Vessel, Pressing and Drying Where Liq. is Fermented to Provide Compost".

Database WPIL, Derwent Publications, Ltd., AN 90-011525, & JP-A-1 291 726, 1989, "Artificial Cultivation of Mushroom-Involves Incubating and Cultivating Seed Culture on Medium Obtd. by Fermentation of Genus . . . Bacillus . . . Microorganism without Antifungal Agent".

*Primary Examiner*—Douglas W. Robinson
*Assistant Examiner*—Deborah K. Ware
*Attorney, Agent, or Firm*—Oblon, Spivak, McClelland, Maier & Neustadt

[57] ABSTRACT

A bacterium belonging to *Bacillus subtilis*. The bacterium being identified as *Bacillus subtilis* FERM BP-3418. In addition the bacterium possesses the capability of decomposing aflatoxin. It is useful as an active ingredient in products such as a fungal growth inhibitor, fermentation promoter, and livestock fattening agent.

1 Claim, No Drawings

PURE CULTURE OF *BACILLUS SUBTILIS* FERM BP-3418

BACKGROUND OF THE INVENTION

1) Field of the Invention

This invention relates to a novel bacterium belonging to *Bacillus subtilis* and also to its usage.

2) Description of Related Art

In a wide range of agricultural businesses, various microbial activities take place with some sort of relevance to the agricultural businesses. This relevance may be advantageous or disadvantageous to the agriculture.

For example, fungi are microorganisms generally called "molds" and can be classified roughly into Phycomycetes, Ascomycetes, Basidiomycetes and imperfect fungi. They include many useful fungi, led by yeast.

However, they also include those present in soil and acting as pathogenic bacteria against crops, like molds, so that it is important for agricultural businesses to inhibit their growth. Further, compost is useful as a fertilizer for crops, Livestock excrement or the like is contained in compost, resulting in the potential problem that the compost may become an offensive odor source by growth of a fungus or a hotbed for the proliferation of a pathogenic fungus. Further, an infectious crop disease induced by a fungus such as a mold has communicability and may totally destroy the crop. There is accordingly an outstanding desire for the development of means for effective inhibition of such infectious diseases.

As a method for inhibiting the growth of a fungus, it has conventionally been known to use various antibacterial agents or bacteriostatic agents. As an antibacterial or bacteriostatic ingredient is decomposed, the above method is accompanied by the drawback that it requires periodic re-application of the antibacterial or bacteriostatic agent. It is also accompanied by the drawback that the antibacterial or bacteriostatic agent may also inhibit activities of other useful microorganisms or may become ineffective due to the occurrence of resistant bacteria.

There is hence an long standing demand for the development of a fungus inhibitor which remains effective over a long time and is free from the troublesome occurrence of resistant bacteria.

Reflecting changes in the living environment and consciousness, on the other hand, the level of demand for the prevention of offensive odor and unpleasant odor is increasing. For example, even to livestock farmers and the like who have been in business for many years, neighboring residents often make a demand for the prevention or reduction of offensive odor or unpleasant odor given off from livestock excrement or the like.

Conventional known deodorizing methods which can be used for the prevention of offensive odor include masking methods, chemical deodorizing methods, physical deodorizing methods, and biological deodorizing methods. In the livestock industry where livestock excrement as an offensive odor source occurs continuously and in large quantity, the effectiveness of a chemical or physical deodorizing method is limited, to say nothing of any masking method. A biological deodorizing method is therefore capturing the interest of researchers, because it causes livestock excrement as an offensive odor source to promptly ferment so that occurrence of offensive odor can be prevented. It is, however, the current situation that no fermentation promoting method has yet been established for the prevention of occurrence of offensive odor from livestock excrement. There are similar problems with respect to old-fashioned toilets of the long drop type and garbage from house kitchens. These problems have also not been solved. Further, lignin which is one of principal components of lignified plant bodies such as wood, bamboo and straw and is a network, high molecular compound accompanied by the problem that its decomposition can be insignificant, thus remaining as waste.

Accordingly, it has been strongly desired to develop a method for promptly fermenting odor sources such as livestock excrement, human excrement and kitchen garbage and even lignin to effectively prevent the occurrent of offensive odor.

Further, one of the greatest concerns of livestock farmers is how to raise healthy livestock so that excellent meat or eggs can be obtained. In reality, however, livestock may not be raised satisfactorily in many instances because they may not take sufficient feed or may not digest the feed sufficiently or may catch disease. For example, if easily fermentable feed is fed in a large quantity at once to a ruminant mammal such as a cow or ox, rumen acidosis takes place temporarily, thereby decreasing its appetite. This trouble then induces an abnormal gastric juice pH of the rumen, damage to the reticulorumen, production of unusual metabolic products such as amines, extraordinary fermentation heat, etc., so that normal digestion and absorption are inhibited. Further, bacteria other than flora may grow extraordinarily and penetrate into blood, thereby causing digestive tract diseases, hepatopathy, motor organ diseases, reproductive difficulties, heat stroke, mastitis, dermatitis, or the like in some instances.

To raise healthy livestock for the provision of livestock products in greater quantity, there has been a strong demand for the development of technology that can promote digestion of feed by livestock and can hence fatten the livestock.

SUMMARY OF THE INVENTION

The present inventors isolated many bacteria from soils and have conducted screening with respect to their properties. As a result, a novel bacterium belonging to *Bacillus subtilis* and having aflatoxin decomposing ability has been found. It has also been found that this bacterium inhibits occurrence of fungi and exhibits excellent fungal growth inhibiting effects, that the use of this bacterium can promote fermentation to effectively decompose even lignin, and that the feeding of this bacterium together with feed to livestock can suppress abnormal fermentation or the like in the digestive tract of livestock and can hence promote the growth of the livestock.

An object of this invention is therefore to provide a bacterium belonging to *Bacillus subtilis* and having aflatoxin decomposing ability.

Another object of this invention is to provide a fungal growth inhibitor comprising the above bacterium as an active ingredient.

A further object of this invention is to provide a fermentation promoter comprising the above bacterium as an effective ingredient.

A still further object of this invention is to provide a livestock fattening agent comprising the above bacterium as an effective ingredient.

The bacterium according to the present invention can be used very advantageously in agricultural fields where microbial activities take place with some sort of relevance.

For example, employment of a fungal growth inhibitor making use of the bacterium of this invention makes it possible to inhibit growth of a fungus, especially a pathogenic mold, so that its application to soil or a plant can prevent crop disease. Further, application of the fungal growth inhibitor to compost or the like can inhibit growth of a pathogenic mold in the compost, thereby making it possible to prevent occurrence of offensive odor which would otherwise take place due to growth of the mold.

Further, application of a fermentation promoter making use of the bacterium according to this invention to livestock excrement or the like can promote extremely effective fermentation so that the fermentation can be brought to completion in 1-2 months as opposed to ½-1 year that has heretofore been required to complete the fermentation. Moreover, practically no offensive odor is given off during the fermentation period. On the other hand, use of the fermentation promoter of this invention in an aeration tank can shorten the waste water treatment time to half the time that conventionally required. In addition, production of offensive odor is reduced and, after the treatment, the BOD and SS values both drop to values about 1/30 or less of the corresponding conventional values. Addition of the fermentation promoter of this invention to sawdust, which is employed as bedding used when raising livestock (in broiler cages, pig houses, or feeder cattle houses), can facilitate the disposal of excrement and can also obviate occurrence of offensive odor. Furthermore, fermentation proceeds continuously in the bedding and, as a result, the bedding is warm even in winter so that occurrence of diseases such as diarrhea and pneumonia, which have heretofore been developed due to abdominal chilling of the livestock, decreases.

In addition, administration of a livestock fattening agent, which makes use of the bacterium of this invention, to livestock enables maintenance of the inside of the digestive tract of the livestock at a normal level so that the absorption of nourishment through the digestive tract can be promoted. As a result, the weight of the livestock can be steadily increased or, for example, the production of eggs can be increased. This is extremely advantageous for the livestock industry.

DETAILED DESCRIPTION OF THE INVENTION AND PREFERRED EMBODIMENTS

The bacterium according to this invention belongs to *Bacillus subtilis* and has aflatoxin decomposing ability. Any bacterium can be used as long as these conditions are met.

Examples of characteristics which these bacteria have will be shown next.

TABLE 1

| Property | B. subtilis |
| --- | --- |
| Swelling of cells | − |
| 7% NaCl | + |
| NO$_3$ → NO$_2$ | + |
| VP reaction | + |
| Egg yolk | − |
| Indole | − |
| 60° C. | − |
| Gram stain | + |

TABLE 1-continued

| Property | B. subtilis |
| --- | --- |
| Location of endospores | Center |
| Gloss | None |
| Colony surface | Wrinkled |

As one example of these bacteria, *Bacillus subtilis* DB9011 found by the present inventors can be mentioned. Its microbial characteristics are as follows:

Morphotype:

A bacillus with 0.7-0.8 μm cell width. Oval endospores are present rather centrally and do not swell cells. Has mobility and forms R colony. No growth under anaerobic conditions.

State of growth on various culture media:

(1) DHL agar medium—No growth.

(2) MacConkey's agar medium—No growth.

(3) Mannitol salt medium—Good growth. Gloss. No wrinkles on colony surface. Colonies have a yellow color.

(4) General agar medium—Good growth. No gloss. Wrinkles on colony surface. Colonies have a white color.

(5) Heart infusion agar medium—Good growth. No gloss. Wrinkles on colony surface. Colonies have a white color.

(6) Blood agar medium (added with 10% sheep blood)—Good growth. No gloss. Wrinkles on colony surface. Colonies have a white color.

(7) PDA medium—Good growth. No gloss. Wrinkles on colony surface. Colonies have a white color.

| Physiological characteristics: | |
| --- | --- |
| Gram stain: | + |
| Gelatin test: | |
| State of growth: | Full surface liquefaction |
| Liquefaction of gelatin: | + |
| Litmus milk: | |
| Reaction: | Acid |
| State: | Coagulated |
| Reduction of nitrates: | + |
| Denitration reaction: | − |
| MR test: | − |
| Production of indole: | − |
| Production of hydrogen sulfide: | − |
| Utilization of citric acid: (Christensen citrate medium) | + |
| Urease: | − |
| Oxidase: | + |
| Catalase: | + |
| Growth range: | |
| pH: | 4-9 |
| Temperature: | 25-50° C. |
| OF test: | Fermented with production of gas (owing glucose decomposition) |

| Utilization of saccharides: | | |
| --- | --- | --- |
| | Gas production | Acid formation |
| L-Arabinose | − | + |
| D-Xylose | − | + |
| D-Glucose | + | + |
| D-Mannose | − | + |
| D-Fructose | − | + |
| D-Galactose | − | + |
| Maltose | − | + |

-continued

| Utilization of saccharides: | | |
|---|---|---|
| | Gas production | Acid formation |
| Sucrose | − | + |
| Lactose | − | + |
| Trehalose | − | + |
| D-Sorbitol | − | + |
| D-Mannitol | − | + |
| Inositol | − | + |
| Glycerin | − | + |
| Starch | − | + |
| Decomposition of esculin | | + |
| Utilization of malonic acid | | − |
| Decomposition of arginine | | + |
| Decarboxylation reaction of lysine | | + |
| Decomposition of urea | | ± |
| Decomposition of aflatoxin | | + |
| Decarboxylation reaction of ornithine | | − |
| Coagulase | | − |
| Hemolysis | | + |
| Tolerance to sodium hydrochloride | | Up to 10% |
| Tolerance to potassium cyanide | | Can grow |
| Lecithinase | | − |

The present inventors determined *Bacillus subtilis* DB9011 as a new cell strain from the various characteristics described above, and deposited it under FERM BP-3418 on May 21, 1991 with the Fermentation Research Institute, Agency of Industrial Science and Technology, Ministry of International Trade and Industry, Government of Japan.

To prepare a fungal growth inhibitor by using the above-described bacterium of this invention, it is necessary to allow the bacterium to grow in a nutrient source such as a vegetable organic substance, defatted rice bran or wheat bran, especially in a vegetable organic substance, and to use the resultant culture liquor either as it is or after filtering it into a water suspension.

When such a water suspension is prepared, it is preferable to control the number of bacterium cells at $10^4$ or more per ml.

Illustrative vegetable organic substances usable for growth include the vegetable organic substance which can be obtained by completely aging waste sawdust used in the artificial cultivation of champignon. When such a vegetable organic substance is used, *Bacillus subtilis* changes from the vegetative form to the propagative form, leading to an increased cell number and, hence, to improved action.

When the fungal growth inhibitor according to this invention is applied to soil, it is generally necessary to apply it at a rate of about $10^9$ per $m^2$ although this application rate varies depending on whether the purpose of the application is to prevent crop disease caused by a fungi as a pathogenic bacterium or to eliminate a pathogenic fungi already present at high concentration.

When the fungal growth inhibitor according to this invention is applied to compost or the like, it is necessary either to apply it to the entire surface of the compost or to thoroughly mix it with the compost. This allows *Bacillus subtilis*, the active ingredient, to grow in the compost, whereby growth of the fungi can be inhibited.

In this case, the application rate of the fungal growth inhibitor can be determined generally by relying, as an approximate standard, upon the elimination of odor from the compost or the like.

To prepare a fermentation promoter by using the bacterium of this invention, it is preferable to have the bacterium of this invention carried on an excipient such as the above-described vegetative organic substance, defatted rice bran or wheat bran, especially on the vegetative organic substance.

In this case, it is preferable to control the number of bacterium cells at $2 \times 10^5$ or more per gram of the excipient.

It is necessary to apply the fermentation promoter according to this invention to the entire surface of an offensive odor source, for example, livestock excrement such as poultry waste, swine excrement or cow/ox feces, human excrement, kitchen garbage or the like or to thoroughly mix the fermentation promoter with the offensive odor source. This can promote fermentation so that production of offensive odor can be prevented. These deodorizing effects can be observed even from the first day after its application and can last 15 days or even longer. For example, where the occurrence of livestock excrement as an offensive odor source is at a constant rate and livestock excrement newly discharged does not deposit on the previous accumulation, surface application at the frequency of once every several months is expected to maintain continuing deodorizing efficacy.

To promote fermentation in an aeration tank, it only necessary to throw the fermentation promoter of this invention into the aeration tank. This can promote fermentation in the aeration tank.

The application rate of the fermentation promoter according to this invention varies depending on the kind, quantity, conditions and the like of the offensive odor source, and cannot be given in a wholesale manner. Although empirical determination is needed, a suitable application rate can generally be determined by using, as an approximate standard, the elimination of odor from the offensive odor source.

Further, to prepare a livestock fattening agent by using the bacterium of this invention, it is necessary to mix the bacterium of this invention as an essential ingredient with, as optional ingredients, other ingredients required for the growth of livestock. Examples of such optional ingredients include defatted rice bran, vegetable organic substances, wheat bran, calcium sources such as fossil shells, brewer's grain, various vitamins, and nourishment.

It is preferable to control the number of bacterium cells at $1 \times 10^5$ or more per gram of the livestock fattening agent.

Preferred examples of the livestock fattening agent according to this invention include the livestock fattening agent which is obtained by mixing defatted rice bran and fossil shells at an appropriate rate, for example, of about 4:1 and then adding *Bacillus subtilis*, at a rate of $1 \times 10^5$ or more per gram of the resulting livestock fattening agent, to the mixture so formed. In such a livestock fattening agent, *Bacillus subtilis* changes from the vegetative form to the propagative form and proliferates using the organic substance as a nourishment, leading to an increased cell number and, hence, to improved action.

The livestock fattening agent according to the present invention can be administered by adding it to livestock feed and then feeding the resultant mixture to livestock. In some instances, however, the livestock fattening agent of this invention can be fed in place of feed. When it is administered together with feed, it can be added generally at a rate of about 0.5–10%, preferably at about 1–5% to feed.

The administration period of the livestock fattening agent of this invention varies depending on the kind, growth stage, fattened extent and the like of the livestock to be administered, and cannot be given in a wholesale manner. It is necessary to determine it empirically.

Although it has not been elucidated yet why each bacterium of this invention can be used for many applications such as fungal growth inhibitors, fermentation promoters and livestock fattening agents, the bacterium is considered to inhibit growth of microorganisms which are present in the environment and give disadvantageous effects—for example, pathogenic fungi, molds which give off offensive odor, and bacteria which produce a growth inhibiting substance such as aflatoxin—so that normal fermentation by a Bacillus bacterium can be promoted.

Described more specifically, the effects of the fungal growth inhibitor are considered attributable to any one of (1) the ability of competitive growth with fungi, (2) the hemolytic action against fungi and (3) the production of a growth inhibiting substance—which the bacterium belonging to *Bacillus subtilis* has—or to their synergism.

Further, the effects of the fermentation promoter are considered attributable to the nature of the bacterium belonging to *Bacillus subtilis* that (1) the bacterium grows in livestock excrement or the like to inhibit growth of offensive-odor-producing molds and (2) the bacterium grows there in place of the molds and decomposes the livestock excrement or the like.

On the other hand, the effects of the livestock fattening agent according to this invention are considered attributable to the nature of the bacterium belonging to *Bacillus subtilis* that (1) the bacterium inhibits growth of noxious bacteria in the digestive tract of livestock, (2) the bacterium grows in place of such noxious bacteria in the digestive tract of livestock and (3) the bacterium decomposes lignin which is contained in feed and is considered to be difficult to decompose.

The above-described effects cannot be obtained at all from any other bacteria including the other types of bacteria belonging to Bacillus.

As has been described above, the bacterium according to this invention is extremely advantageous from the standpoint of agricultural business.

The present invention will hereinafter be described in further detail by the following examples. It should however be borne in mind that the present invention is by no means limited to or by the following examples.

TEST 1

Slant media of PDA agar were prepared, to which the below described fungi were inoculated, respectively. They were then cultured at 25-28° C. for 7-10 days, during which most of the fungi formed spores. The formed spores were suspended at $1 \times 10^6$ cells/ml in physiological saline or phosphate buffer to which a surfactant had been added, so that a spore suspension was formed. To a PDA agar medium plate (in a Petri dish of 90 mm in diameter) which had been prepared on the side, the spore suspension was dropped in an amount of 0.1 ml per plate and then spread evenly by a spreader to have it absorbed sufficiently in the medium. A bacillus suspension prepared at $10^6$ cells/ml was centrally inoculated at one spot (about 25 μl) on the medium. The bacillus was then cultured at 25°-28° C. for 5-10 days to observe the formation of any inhibited circular area.

As a result, *Bacillus subtilis* DB-9011 inhibited the growth of each fungus.

| Mold used | |
| --- | --- |
| Helicobasidium mompa | IFO 31651 |
| Rosellinia necatrix | IFO 9420 |
| Vaisa ceratosperma | IFO 30252 |
| Phytophthora infestans | IFO 9174 |
| Botrytis cinerea | IFO 31831 |
| Helicobasidium mompa | Collected from apple tree roots |
| Rosellinia necatrix | Collected from pear tree roots |
| Vaisa ceratosperma | Collected from peach tree roots |
| Asperigillus niger | Collected from peach tree roots |
| Asperigillus ochraceus | Strain stored at AHC Inc. |
| Asperigillus flavus | Aflatoxin-producing strain |
| Asperigillus flavus | Strain stored at AHC Inc. |
| Asperigillus fumigatus | Collected from fowl lungs |
| Aureobasidium pullulans | Collected from soil |
| Fusarium oxysporum | Collected from cucumber |

EXAMPLE 1

Waste sawdust, which had been used in the artificial cultivation of champignon and had been completely aged, was added with $2 \times 10^5$ cells/g-sawdust of *Bacillus subtilis* DB-9011 (FERM BP-3418), whereby a fungal growth inhibitor was prepared (Invention Product 1).

EXAMPLE 2

After the Invention Product 1 of Example 1 was stored for 10 days at about 20° C., 100 g of the product were suspended in 1,000 ml of water. The suspension was thoroughly stirred, followed by filtration. The filtrate was provided as a liquid fungal growth inhibitor (Invention Product 2). The Invention Product 2 contained $1 \times 10^4$ cells of *Bacillus subtilis* DB-9011 per ml.

EXAMPLE 3

A peach tree which had died of "mompa" disease caused by parasitism of a fungus, specifically *Helicobasidium mompa* or *Rosellinia necatrix* was pulled out of the ground. Two kilograms of the Invention Product 1 were spread there and fully mixed with the soil. A young peach tree was newly planted there. Seven months after the transplant, the peach tree fully struck roots into the soil. Its growth was also very energetic.

When a peach tree dies of "mompa" disease, pathogenic mold is present at high concentration in the soil so that a young tree, if newly planted there, will be killed promptly. In general, it is therefore said that a new young tree cannot be planted until three years have elapsed.

EXAMPLE 4

In a cucumber field where damping-off had occurred for root-knot nematode disease, the Invention Product 1 was applied at a rate of 100 g per plant by placing it into several holes bored around the roots of each plant.

Even from damped-off plants, new shoots began to grow from one week after the application and tendrils grew progressively to regain vitality.

EXAMPLE 5

In an apple farm affected severely by canker (fungus disease), effects of the fungal growth inhibitor according to this invention was investigated. After canker-affected branches were cut off, the Invention Product 2 was sprayed onto all the apple trees at an application rate of 10 liters per tree. As a result, there was no tree affected by canker after the application. Further, the trees already affected by canker regained vitality.

EXAMPLE 6

Effects of the fungal growth inhibitor of this invention were investigated in a PVC-film-covered green house in which gray mold had occurred. Cucumber plants which were visually found to be affected by gray mold were pulled out, and the Invention Product 2 was spread there at an application rate such that its application rate was 800 ml per $m^2$ of the whole green house.

As a result, gray mold no longer occurred to influence the yield. Incidentally, the yield of cucumbers usually drops to a significantly low level upon outbreak of this disease.

EXAMPLE 7

With respect to the fungal growth inhibitor according to this invention, its growth and toxin-production inhibiting effects were investigated in the following manner against *Aspergillus flavus* NRRL 2999, which shows aflatoxin-producing ability. Preparation of antifungal preparation:

Employed was an antifungal preparation (Antifungal Preparation 3), which had been obtained by subjecting one inoculating loopful of *Bacillus subtilis* DB-9011 to shaking culture for 24 hours in 100-ml brain heart infusion and then diluting the resultant culture tenfold in water.

Results of Experiments (1) Test in Culture Bottle

After potato dextrose agar medium (PDA medium) was placed in a test culture bottle and solidified, 1 g of corn flour and $10^6$ cells of a test bacterium were added to the medium. One drop (about 30 $\mu$l) of the Antifungal Preparation 3 was added to the test culture bottle, followed by culture at about 30° C. On the fourth and sixth days after the initiation of the culture, growth of *Aspergillus flavus* and any other fungi was investigated. As a result, growth of fungi including *Aspergillus flavus* was not observed in the culture bottle in which the Antifungal Preparation 3 was added dropwise. In Control, in which the Antifungal Preparation 3 was not added, growth of hyphae of *Aspergillus flavus* and formation of its condinia were observed conversely, and growth of other fungi was also observed there.

(2) Test in Petri Dish

On PDA medium solidified in a Petri dish, 0.5 g of a test feed sample was placed and $10^6$ of the test fungus were inoculated. One drop (about 25 $\mu$l) of the Antifungal Preparation 3 was then added, followed by culture at about 30° C. On the fourth and sixth days after the initiation of the culture, growth of *Aspergillus flavus* and any other fungi was investigated. The results are tabulated next.

| Test feed | State of growth of fungi |
|---|---|
| Formula feed A* | Occurrence of fungi was not observed. |
| Formula feed B* | Occurrence of fungi was not observed. |
| Corn | Occurrence of fungi was not observed. |
| None (on culture medium) | Occurrence of fungi was not observed. |

*Formula feed A   Raising feed for mature fowl.
*Formula feed B   Fattening feed for weaner pigs.

Incidentally, when the Antifungal Preparation 3 was not dropped, growth of hyphae of *Aspergillus flavus* and formation of its condinia were observed in each of the test feeds, and growth of other fungi was also observed there.

(3) Inhibition of Formation of Aflatoxin

After the culture described above under (1) was continued for 17 days after the initiation of the culture, the resulting culture was extracted twice with 50-ml portions of chloroform, respectively. The extract was concentrated to 2 ml and then subjected to thin layer chromatography to determine whether aflatoxin had been formed or not.

As a result, production of aflatoxin $B_1$ and $G_1$ was observed in Control but was not observed in the culture bottle in which the Antifungal Preparation 3 was used.

EXAMPLE 8

Waste sawdust, which had been used in the artificial cultivation of champignon and had been completely aged, was added with $2 \times 10^5$ cells/g-sawdust of *Bacillus subtilis* DB-9011, whereby a fermentation promoter was prepared (Invention Product 4).

EXAMPLE 9

Three grams of the Invention Product 4 obtained in Example 8 were spread over the entire surface of 100 g of fowl waste. As a result, the fowl waste was completely fermented in 30–45 days although its complete fermentation had conventionally been considered to take 6 months to 1 year. Compared with fowl waste not spread with the invention product, production of offensive odor was much less. Similar effects were observed when swine excrement or bovine excrement was used.

EXAMPLE 10

Sixty kilograms of the Invention Product 4 were added to a 25-ton aeration tank which was designed for the treatment of swine excrement from a pig farm (operation scale: 1,000 pigs). The water temperature in the aeration tank was 22° C. when the invention product was added. On the following day, the water temperature rose to 28° C., and occurrence of water vapor which had not occurred before was observed. Further, the offensive odor had been improved considerably.

Further, the BOD and SS values in the aeration tank was 800 mg/l and 25,000 mg/l before the invention product was added. One month after the addition, they had been improved to 26 mg/l and 20 mg/l, respectively.

EXAMPLE 11

The Invention Product 4 (150 kg) was added to one aeration tank at a pig farm (operation scale: 6,000 pigs), namely, a 5-ton aeration tank. One day after the addition, the offensive odor of the test aeration tank was substantially reduced. Further, occurrence of foams was observed although such foams were not observed with any bacterium used previously. It was hence confirmed that fermentation was under way.

EXAMPLE 12

After 200 l of the contents (70% urine and 30% excrement) of a 400-l privy of the long drop type were stirred well, the Invention Product 4 (1 kg) was added followed by further stirring. Although intense offensive odor was semlled before the addition, this changed to sewer-like odor four days later. Seven days later, the odor level was reduced to such an extent that offensive odor was slightly smelled only in the waste pot. Ten days later, offensive odor was completely eliminated.

Thereafter, occurrence of offensive odor was not recognized even after one month had elapsed.

EXAMPLE 13

After the contents of a 400-l toilet of the long drop type were completely sucked out by a tank truck, 1 kg of the Invention Product 4 was spread evenly. The toilet was observed for 1 month immediately after the spreading of the invention product. During that period, occurrence of offensive odor was not recognized.

EXAMPLE 14

Kitchen garbage, which had been left over for 1 week and gave off very offensive odor, was placed in a supermarket plastic bag, and four handfuls of the Invention Product 4 were added. Three days after the addition, the offensive odor turned to sweat-sour odor and, one week after the addition, raw vegetables were completely decomposed into liquid.

EXAMPLE 15

The Invention Product 4 (100 g) was added to a 15-l home garbage pail which was 20% full with kitchen garbage. Offensive odor was eliminated eight hours after the addition. No offensive odor was given off even when the pail was filled to 60%.

EXAMPLE 16

As bedding for two pig pens out of 14 pig pens at a pig farm (operation scale: 1,500 pigs), one ton of sawdust with 3% of the Invention Product 4 added was used. It was laid to a thickness of 20 cm. From the following day, offensive odor was eliminated in those pig pens and, moreover, the bedding was not dried but retained a suitable water content so that the bedding did not give off dust. Further, the sawdust fermented and maintained a suitable temperature, whereby the pigs did not develop chill-related diarrhea. From the third week of the test, the color of swine excrement changed and no offensive odor was given off even from fresh swine excrement (probably because the pigs in the test pig pens ate the Invention Product 4 contained in the bedding).

In contrast, offensive odor and dust were given off in a control pig pen where sawdust alone was used as bedding.

Further, the bedding of the test pig pens after the sales of the pigs did not give off offensive odor and, when piled up, promptly fermented so that it was successfully used again as bedding after the completion of the fermentation.

EXAMPLE 17

To a mixture consisting of 80% defatted rice bran and 20% fossil shells, *Bacillus subtilis* DB-9011 (FERM BP3418) was added at a rate of $1 \times 10^5$ cells per gram of the mixture, whereby a livestock fattening agent was prepared (Invention Product 5).

EXAMPLE 18

Test media were prepared by adding 0.5 mM of α-naphthol and 0.1% of p-cresol to portions of potato agar medium, respectively. Those test media were inoculated with *Bacillus subtilis* DB-9011, followed by culture for 5–10 days. The test medium added with α-naphthol was stained purple so that the formation of laccase was confirmed. On the other hand, the test medium added with p-cresol was stained brown so that excretion of tyrosinase was confirmed. From these results, the present cell strain has been confirmed to have lignin decomposing ability.

EXAMPLE 19

To a feed, the Invention Product 5 was added at a rate of 3%. The resulting feed was fed to dairy cattle for 1 month. As a result, whichever livestock fattening agent was added, the milk yield of the dairy cattle increased by about 5% compared with the milk yield when the livestock fattening agent was not added. Further, problems such as reproductive difficulties did not occur so that effects for the prevention of such problems have been confirmed.

EXAMPLE 20

Using 10 broiler chickens (species: Kobu) per group, effects of the livestock fattening agent of this invention for chickens were investigated. Established first were a test group for a feed added with 3% of the Invention Product 5 and another test group (control group) for the feed alone. The broiler chickens in each group were raised for 3 weeks, and their average body weight was measured. As a result, the average body weight of the chickens in the test group in which the livestock fattening agent of this invention was administered was found to be heavier by 150 g than that of the chickens in the control group. According to the results of a pathological examination, no intestinal abnormality was observed on any of the chickens in the test group but, in the control group, petechial bleeding or hyperemia was observed on the duodenum and jejunum of each of the ten chickens. Further, the length of the intestinal tract of each chicken in the test group was 1.5 times as long as that in the control group, thereby indicating more active digestion and absorption. Substantially the same effects were obtained when the Invention Product 2 was used.

EXAMPLE 21

Using 10 laying fowls (species: Dekalb TX; age: 143 days) per group, egg laying rate improving effects by the administration of the livestock fattening agent of this invention were investigated. Established were a test group for a feed added with 3% of the Invention Product 5 (3% group), another test group for the feed added with 10% of the Invention Product 5 (10% group) and a further group for the feed alone (control group). The test ran for 2 months, and the egg laying rate observed during that period. The results are shown in Table 2. Incidentally, the feeding was ad libitum feeding and various vaccines were inoculated as usual.

TABLE 2

| Test group | Egg laying rate during test period | Egg laying rate per week* |
| --- | --- | --- |
| 3% Group | 62.1 | 97.1 |
| 10% Group | 59.0 | 90.0 |
| Control group | 54.2 | 82.9 |

*Egg laying rate per week: Egg laying rate during 1 week before the completion of the test.

As is evident from the above results, the egg laying rate of laying fowls was increased when the livestock fattening agent of this invention was employed. Although no differences were observed among the three groups in the body weight increase of the layers during the test period and the results of the pathological examination, the intake of the feed was greater by about 25 g/day per layer in the 3% group and by about 2 g/day per layer in the 10% group, both higher than the intake of the feed by the layers in the control group.

I claim:

1. A biologically pure culture of *Bacillus subtilis* FERM BP-3418.

* * * * *